(12) United States Patent
Smith et al.

(10) Patent No.: US 8,832,927 B2
(45) Date of Patent: Sep. 16, 2014

(54) METHOD OF MANUFACTURING SURGICAL ANTENNAS

(75) Inventors: Ian Smith, Boulder, CO (US); Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 289 days.

(21) Appl. No.: 13/351,463

(22) Filed: Jan. 17, 2012

(65) Prior Publication Data

US 2012/0110834 A1    May 10, 2012

Related U.S. Application Data

(62) Division of application No. 12/401,268, filed on Mar. 10, 2009, now Pat. No. 8,118,808.

(51) Int. Cl.
| | |
|---|---|
| *H01P 11/00* | (2006.01) |
| *A61B 18/18* | (2006.01) |
| *H01Q 9/16* | (2006.01) |
| *A61N 5/04* | (2006.01) |
| *A61B 18/00* | (2006.01) |

(52) U.S. Cl.
CPC ............... *A61B 18/18* (2013.01); *A61N 5/045* (2013.01); *H01Q 9/16* (2013.01); *A61B 18/1815* (2013.01); *A61B 2018/1838* (2013.01); *A61B 2018/00023* (2013.01)
USPC ................. 29/600; 29/594; 29/601; 343/790; 606/33

(58) Field of Classification Search
USPC ................. 29/25.35–25.42, 605–606, 592.1; 361/311–312, 323; 606/31–33, 606/103–105
See application file for complete search history.

(56) References Cited

U.S. PATENT DOCUMENTS

| | | |
|---|---|---|
| 3,634,606 A | 1/1972 | Iyengar |
| D223,367 S | 4/1972 | Kountz |
| 3,870,047 A | 3/1975 | Gonser |
| 3,885,083 A | 5/1975 | Jachimowicz et al. |
| D263,020 S | 2/1982 | Rau, III |
| D266,842 S | 11/1982 | Villers et al. |
| D278,306 S | 4/1985 | McIntosh |
| 4,583,589 A | 4/1986 | Kasevich |
| 4,643,186 A | 2/1987 | Rosen et al. |
| 4,658,836 A | 4/1987 | Turner |
| 4,676,258 A | 6/1987 | Inokuchi et al. |
| 4,691,703 A | 9/1987 | Auth et al. |
| 4,700,716 A | 10/1987 | Kasevich et al. |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern, Copy attached.

(Continued)

*Primary Examiner* — Minh Trinh

(57) ABSTRACT

A method of manufacturing a surgical antenna includes bonding a trocar screw and a conductor together and overmolding the trocar screw with a puck material to form a puck assembly. A trocar is coupled to the trocar screw, which forms a distal radiating section, and a proximal antenna member is coupled to the puck assembly, which forms a proximal radiating section.

7 Claims, 5 Drawing Sheets

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| 4,776,086 A | 10/1988 | Kasevich et al. |
| 5,257,635 A | 11/1993 | Langberg |
| 5,370,676 A | 12/1994 | Sozanski et al. |
| 5,370,677 A | 12/1994 | Rudie et al. |
| D354,218 S | 1/1995 | Van de Peer |
| 5,599,295 A | 2/1997 | Rosen et al. |
| 5,720,718 A | 2/1998 | Rosen et al. |
| 5,974,343 A | 10/1999 | Brevard et al. |
| 6,047,216 A | 4/2000 | Carl et al. |
| D424,693 S | 5/2000 | Pruter |
| D424,694 S | 5/2000 | Tetzlaff et al. |
| D425,201 S | 5/2000 | Tetzlaff et al. |
| 6,206,876 B1 | 3/2001 | Levine et al. |
| 6,210,367 B1 | 4/2001 | Carr |
| 6,223,086 B1 | 4/2001 | Carl et al. |
| 6,230,060 B1 | 5/2001 | Mawhinney |
| D449,886 S | 10/2001 | Tetzlaff et al. |
| D457,958 S | 5/2002 | Dycus et al. |
| D457,959 S | 5/2002 | Tetzlaff et al. |
| 6,427,089 B1 | 7/2002 | Knowlton |
| 6,496,736 B1 | 12/2002 | Carl et al. |
| 6,496,738 B2 | 12/2002 | Carr |
| 6,544,264 B2 | 4/2003 | Levine et al. |
| 6,652,520 B2 | 11/2003 | Moorman et al. |
| D487,039 S | 2/2004 | Webster et al. |
| 6,706,040 B2 | 3/2004 | Mahon et al. |
| D496,997 S | 10/2004 | Dycus et al. |
| D499,181 S | 11/2004 | Dycus et al. |
| 6,878,147 B2 | 4/2005 | Prakash et al. |
| D525,361 S | 7/2006 | Hushka |
| D531,311 S | 10/2006 | Guerra et al. |
| 7,128,739 B2 | 10/2006 | Prakash et al. |
| D533,942 S | 12/2006 | Kerr et al. |
| 7,147,632 B2 | 12/2006 | Prakash et al. |
| D535,027 S | 1/2007 | James et al. |
| D541,418 S | 4/2007 | Schechter et al. |
| D541,938 S | 5/2007 | Kerr et al. |
| 7,226,446 B1 | 6/2007 | Mody et al. |
| 7,234,977 B2 | 6/2007 | Westlund et al. |
| 7,244,254 B2 | 7/2007 | Brace et al. |
| 7,276,061 B2 | 10/2007 | Schaer et al. |
| 7,311,703 B2 | 12/2007 | Turovskiy et al. |
| 7,318,824 B2 | 1/2008 | Prakash et al. |
| D564,662 S | 3/2008 | Moses et al. |
| D576,932 S | 9/2008 | Strehler |
| 7,527,623 B2 | 5/2009 | Prakash et al. |
| D594,736 S | 6/2009 | Esjunin |
| D594,737 S | 6/2009 | Kelly et al. |
| 7,594,313 B2 | 9/2009 | Prakash et al. |
| D606,203 S | 12/2009 | Husheer et al. |
| D613,412 S | 4/2010 | DeCarlo |
| 7,862,559 B2 | 1/2011 | Prakash et al. |
| D634,010 S | 3/2011 | DeCarlo |
| 8,035,570 B2 | 10/2011 | Prakash et al. |
| 8,069,553 B2 * | 12/2011 | Bonn ........................... 29/600 |
| 8,118,808 B2 * | 2/2012 | Smith et al. .................... 606/33 |
| 2003/0109868 A1 | 6/2003 | Chin et al. |
| 2005/0149010 A1 | 7/2005 | Turovskiy et al. |
| 2005/0245920 A1 | 11/2005 | Vitullo et al. |
| 2006/0085054 A1 | 4/2006 | Zikorus et al. |
| 2006/0259024 A1 | 11/2006 | Turovskiy et al. |
| 2006/0264923 A1 | 11/2006 | Prakash et al. |
| 2006/0282069 A1 | 12/2006 | Prakash et al. |
| 2006/0293650 A1 | 12/2006 | Prakash et al. |
| 2007/0203480 A1 | 8/2007 | Mody et al. |
| 2007/0203551 A1 | 8/2007 | Cronin et al. |
| 2007/0219546 A1 | 9/2007 | Mody et al. |
| 2008/0308256 A1 | 12/2008 | Deborski et al. |
| 2009/0264877 A1 | 10/2009 | DeCarlo |
| 2010/0082082 A1 | 4/2010 | Prakash et al. |
| 2010/0234839 A1 | 9/2010 | Smith et al. |
| 2010/0298822 A1 | 11/2010 | Behnke |
| 2011/0060325 A1 | 3/2011 | Bonn |
| 2011/0071511 A1 | 3/2011 | Brannan et al. |
| 2011/0077634 A1 | 3/2011 | Brannan |
| 2011/0238054 A1 | 9/2011 | Kim et al. |
| 2011/0238055 A1 | 9/2011 | Kim et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| EP | 1 186 274 | 4/2006 |
| EP | 2 253 286 | 11/2010 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |

(56) References Cited

FOREIGN PATENT DOCUMENTS

| | | |
|---|---|---|
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO95/18575 | 7/1995 |
| WO | WO00/048672 | 8/2000 |
| WO | WO03/039385 | 5/2003 |
| WO | WO2008/043999 | 4/2008 |
| WO | WO2010/035831 | 4/2010 |

OTHER PUBLICATIONS

U.S. Appl. No. 08/483,742, filed Jun. 7, 1995, Roger A. Stern, Copy attached.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,1850, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.

(56) References Cited

OTHER PUBLICATIONS

Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, Vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659- 662, Sep. 1983.
Joseph Ortenberg, " LigaSurem™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.

(56) References Cited

OTHER PUBLICATIONS

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'"Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.

(56) References Cited

OTHER PUBLICATIONS

European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

* cited by examiner

METHOD OF MANUFACTURING SURGICAL ANTENNAS

CROSS-REFERENCE TO RELATED APPLICATIONS

This application is a divisional application of U.S. patent application Ser. No. 12/401,268, now U.S. Pat. No. 8,118,808, entitled "Cooled Dielectrically Buffered Microwave Dipole Antenna" filed on Mar. 10, 2009 and hereby incorporated by reference in its entirety.

BACKGROUND

1. Technical Field

The present disclosure relates generally to microwave surgical devices having a microwave antenna which may be inserted directly into tissue for diagnosis and treatment of diseases. More particularly, the present disclosure is directed to a microwave antenna having a cooled distal tip and a method of manufacturing the same.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

At the beginning of an ablation procedure, the water content of targeted or surrounding tissue may desirably enhance the dielectric coupling between a microwave antenna and surrounding tissue. However, as ablation proceeds, the water content of surrounding tissue may decrease due to, for example, thermal desiccation or dehydration, which negatively affects dielectric coupling between a microwave ablation antenna and targeted or surrounding tissue. In certain instances, uneven or undesirable ablation patterns may form as a result thereof, which may lead to uneven or incomplete heating within the targeted tissue, which may, in turn, lead to complications and impaired operative outcomes. Further, many types of malignancies are difficult to reach and treat using non-invasive techniques or by using invasive antenna probes designed to be inserted into a normal body orifice, e.g., an easily accessible body opening. These types of conventional probes may be more flexible and may also avoid the need to separately sterilize the probe; however, they are structurally weak and typically require the use of an introducer or catheter to gain access to within the body. Moreover, the addition of introducers and catheters necessarily increase the diameter of the incision or access opening into the body thereby making the use of such probes more invasive and further increasing the probability of any complications that may arise.

Structurally stronger invasive probes exist and are typically long, narrow, needle-like antenna probes which may be inserted directly into the body tissue to directly access a site of a tumor or other malignancy. Such rigid probes generally have small diameters that aid not only in ease of use but also reduce the resulting trauma to the patient. A convenience of rigid antenna probes capable of direct insertion into tissue is that the probes may also allow for alternate additional uses given different situations. However, such rigid, needle-like probes may experience difficulties in failing to provide uniform patterns of radiated energy; and may fail to provide uniform heating axially along and radially around an effective length of the probe. Accordingly, it may be difficult to otherwise control and direct the heating pattern when using such probes.

Additionally, a dielectric junction used to separate portions of a rigid probe may be subjected to bending, compression, and rotational forces during manufacture, and during use. These forces may lead to failure of the junction, particularly where the dielectric junction includes an integrally formed coupling member, such as a threaded or ribbed section. This effect is exacerbated by the structural properties of conventional dielectric materials, such as porcelain or other ceramic materials, which tend to be brittle.

SUMMARY

The present disclosure provides a surgical microwave antenna assembly, methods of use therefor, e.g., in microwave antenna assemblies used in tissue ablation applications, and methods of manufacture thereof. In some variations, the microwave antenna assembly has proximal and distal radiating portions. A coupler, or puck, may be a junction member that couples the proximal and distal radiation sections. At least a portion of the coupler may be disposed between the proximal and distal radiating portions. The distal end of the distal radiating portion may include a trocar having a tapered end which terminates at a tip configured to allow for the direct insertion into tissue with minimal resistance. An inner and an outer conductor extend through the proximal radiating portion, with the inner conductor disposed within the outer conductor. The inner conductor may extend through a channel disposed longitudinally in the coupler assembly. The inner conductor may further extend at least partially into the distal radiating portion. The microwave antenna assembly includes a coolant chamber disposed within the trocar that is configured to receive a cooling fluid, such as water, via a coolant inflow tube in fluid communication with a source of cooling fluid. The microwave antenna assembly may also be connected to a source of microwave energy.

The puck may be formed from elastomeric or ceramic dielectric material. In some embodiments, the puck may be formed from an unbreakable thermoplastic elastomer, such as without limitation, polyether block amide, such as Pebax®, manufactured by The Arkema Group of Colombes, France; polyetherimide (PEI), such as Ultem® and/or Extem®, manufactured by SABIC Innovative Plastics of Saudi Arabia; polyimide-based polymer, such as Vespel®, manufactured by E. I. du Pont de Nemours and Company of Wilmington, Del., United States. In some embodiments, the puck may be formed from ceramic. In some embodiments, tension is applied to the inner conductor, which in turn places the puck in a state of compression, resulting in improved strength and stiffness of the antenna assembly.

The proximal and distal radiating portions may include a dielectric coating formed from, for example without limitation, a heat resistant ceramic material such as titanium dioxide and/or zirconium dioxide. During a microwave ablation procedure, desiccation of target and/or surrounding tissue may adversely affect the electrical properties at the surgical site, including without limitation, causing impedance mismatching and/or undesirable ablation volumes. The dielectric coating may reduce the detrimental effects of tissue desiccation on the ablation process, and may improve operative outcomes and decrease patient recovery times.

In an embodiment according to the present disclosure, a surgical antenna assembly includes a coaxial feedline having an inner conductor, an outer conductor, and a dielectric disposed therebetween. A trocar screw having a distal threaded section and a cylindrical proximal section is operably electrically coupled to a distal end of the inner conductor. The cylindrical proximal section may include a threaded section. A puck is integrally formed with the trocar screw cylindrical proximal section, by, for example without limitation, overmolding, to form the trocar screw/puck subassembly. The surgical antenna assembly includes an electrically conductive distal radiating section having a distal tapered end and a proximal cylindrical end. In embodiments, the distal radiating section has a generally cylindroconical shape. A cooling chamber is defined within the distal radiating section, having an opening to the proximal end of the distal radiating section and having a threaded section into which is threaded the trocar screw. The disclosed antenna includes a proximal radiating section operably coupled to the outer conductor of the feedline. The proximal radiating section may have a generally cylindrical shape. Additionally or alternatively, the proximal radiating section may have a generally square or hexagonal cross sectional shape. The inner conductor is placed under tension and fastened, which draws together the distal radiating section, the trocar screw/puck subassembly, and the proximal radiating section, to form the antenna assembly. In an embodiment, a tensioning mechanism is generally coupled to the inner conductor. Movement of the tensioning mechanism draws the distal radiating section, the puck, and the proximal radiating section under compression to stiffen the antenna assembly.

In an embodiment, the puck includes a distal puck section, a central puck section, and a proximal puck section. The outer diameter of the central puck section is greater than that of at least one of the outer diameter of the distal puck section and the outer diameter of the proximal puck section. The outer diameter of the central puck section is about equal to the outer diameter of the proximal cylindrical end of the distal radiating section and/or the outer diameter of the proximal radiating section.

In an embodiment, the disclosed surgical antenna includes an outer jacket surrounding at least one of the distal radiating section, the puck, and the proximal radiating section. The outer jacket is formed from polytetrafluoroethylene (PTFE), such as Teflon®, or any suitable lubricious polymer such as polyethylene terephthalate (PET) or polyimide. The outer jacket may enable the antenna assembly to more easily penetrate tissue by reducing friction between the shaft and tissue, and/or by inhibiting the adhesion of biomaterials to the shaft.

Also disclosed is a method for manufacturing a surgical antenna. The disclosed method includes the steps of providing a trocar screw adapted to receive a conductor at the proximal end thereof and bonding a conductor to the trocar screw to form a trocar screw subassembly. The conductor may be coupled to the trocar screw using any suitable manner of electrically-conductive bonding, for example without limitation, welding, brazing, soldering, and crimping. The trocar screw subassembly may then be positioned into a mold that is configured to overmold a puck on the trocar screw subassembly. Puck material, for example and without limitation, Pebax®, Ultem®, Extem®, Vespel® and/or ceramic, is injected into the mold and allowed to set, forming a puck assembly. The puck assembly is released from the mold. A trocar adapted at the proximal end thereof to couple to the trocar screw is provided, and coupled to the trocar screw (e.g., by screwing the trocar onto the trocar screw) to form a distal radiating section. A proximal antenna member adapted at the distal end thereof to couple to the puck assembly is provided, and coupled to the puck assembly such that the conductor passes longitudinally through the proximal antenna member and exits at a proximal end thereof. The conductor is tensioned to draw together the distal radiating section, puck assembly, and proximal antenna member under compression to form an antenna assembly, and the conductor is fixed in relation to the proximal antenna member in order to maintain the stiffness of the antenna assembly.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
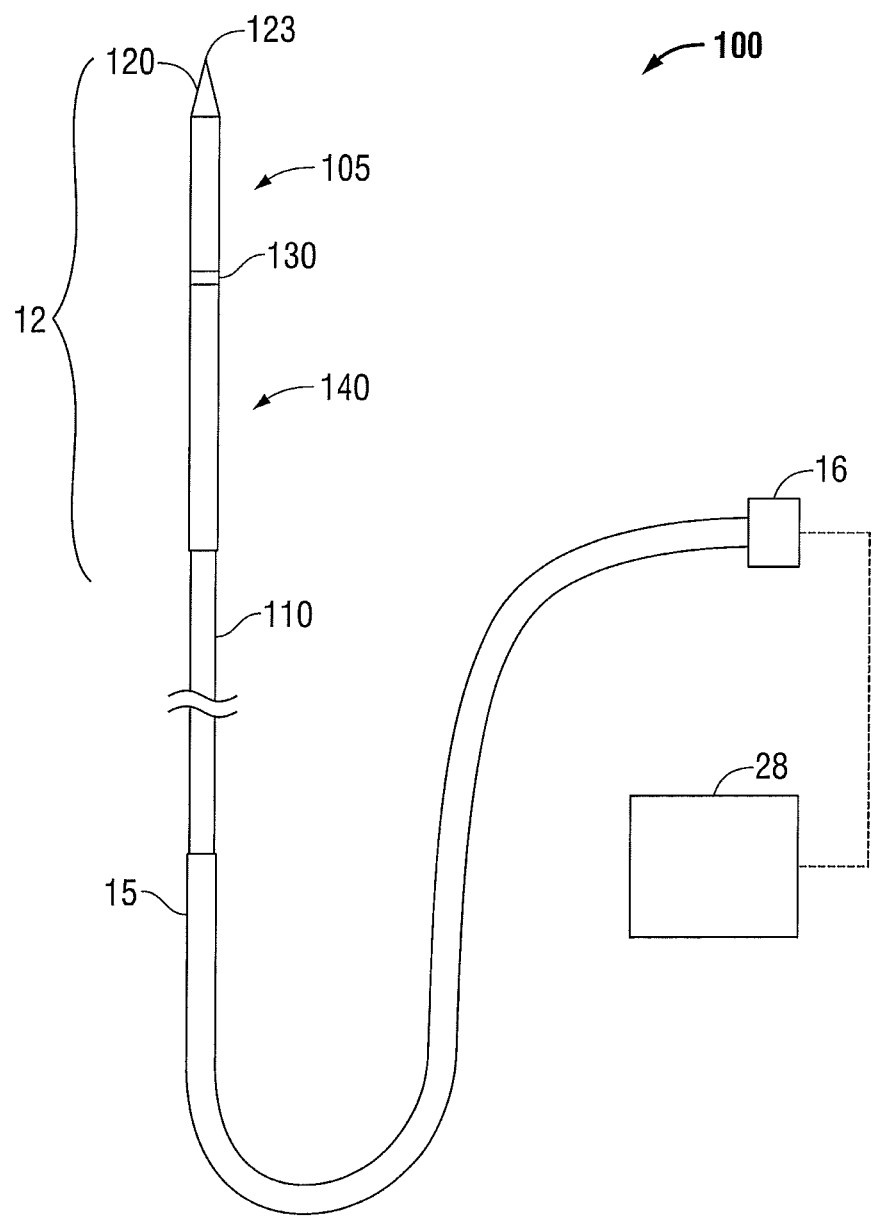
FIG. 1 shows a representative diagram of a variation of a microwave antenna assembly in accordance with an embodiment of the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

FIG. 1 shows an embodiment of a microwave antenna assembly 100 in accordance with the present disclosure. The antenna assembly 100 includes a radiating portion 12 that is connected by feedline 110 (or shaft) via cable 15 to connector 16, which may further connect the assembly 10 to a power generating source 28, e.g., a microwave or RF electrosurgical generator. Assembly 100, as shown, is a dipole microwave antenna assembly, but other antenna assemblies, e.g., monopole or leaky wave antenna assemblies, may also utilize the principles set forth herein. Distal radiating portion 105 of radiating portion 12 includes a tapered end 120 which terminates at a tip 123 to allow for insertion into tissue with minimal resistance. It is to be understood, however, that tapered end 120 may include other shapes, such as without limitation, a tip 123 that is rounded, flat, square, hexagonal, or cylindroconical.

Figure 2:
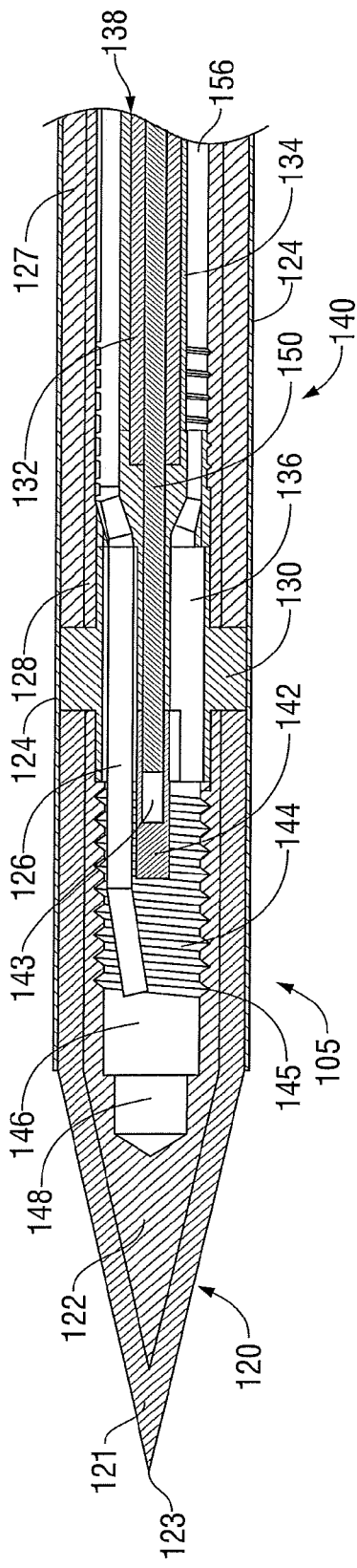
FIG. 2 shows an cross-sectional view of a representative variation of a distal end of microwave antenna assembly in accordance with an embodiment of the present disclosure.
Figure 3:
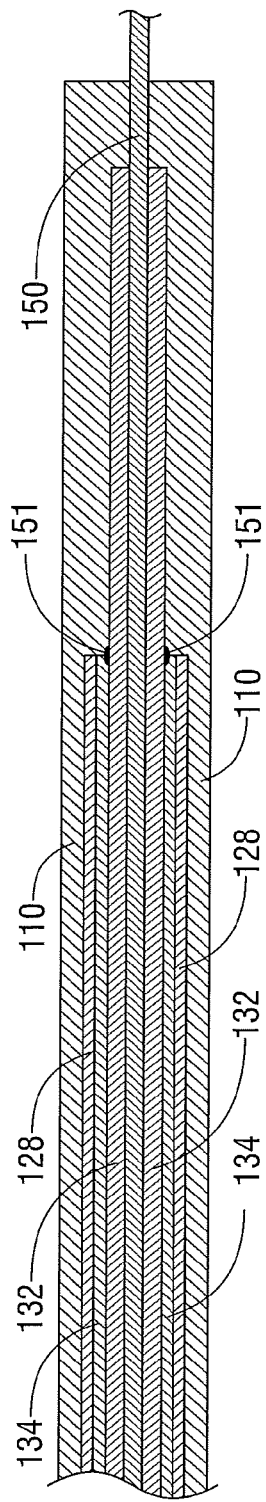
FIG. 3 shows a cross-sectional view of a representative variation of a proximal end of microwave antenna assembly in accordance with an embodiment of the present disclosure.

An insulating puck 130 is disposed between distal radiating portion 105 and proximal radiating portion 140. Puck 130 may be formed from any suitable elastomeric or ceramic dielectric material by any suitable process. In embodiments, the puck 130 is formed by overmolding from polyether block amide (e.g., Pebax®), polyetherimide (e.g., Ultem® and/or Extem®), polyimide-based polymer (e.g., Vespel®), or ceramic. As best illustrated in FIG. 2, puck 130 includes coolant inflow port 131 and coolant outflow port 133 to respectively facilitate the flow of coolant into, and out of, coolant chamber 148 of trocar 122 as further described hereinbelow.

With reference now to FIGS. 2, 3, and 4A-4D, distal radiating portion 105 includes a trocar 122 having a generally cylindroconical shape. Proximal radiating portion 140 includes a proximal antenna member 128 having a generally cylindrical shape. Additionally or alternatively, proximal antenna member 128 may have a generally square or hexagonal shape. Trocar 122 and proximal antenna member 128 may be formed from a variety of biocompatible heat resistant conductive material suitable for penetrating tissue, such as without limitation, stainless steel. Antenna assembly 110 includes a coaxial transmission line 138 having, in coaxial disposition, an inner coaxial conductor 150, an intermediate coaxial dielectric 132, and an outer coaxial conductor 134. Nominally, coaxial transmission line 138 has an impedance of about 50 ohms. Inner coaxial conductor 150 and outer coaxial conductor 134 may be formed from any suitable electrically conductive material. In some embodiments, inner coaxial conductor 150 is formed from stainless steel and outer coaxial conductor 132 is formed from copper. Coaxial dielectric 132 may be formed from any suitable dielectric material, including without limitation, polyethylene terephthalate, polyimide, or polytetrafluoroethylene (PTFE) (e.g., Teflon®, manufactured by E. I. du Pont de Nemours and Company of Wilmington, Del., United States). Inner coaxial conductor 150 is electrically coupled with trocar 122. Outer coaxial conductor 134 is electrically coupled to proximal antenna member 128.

A longitudinal opening 146 within trocar 122, and open to a proximal end thereof, defines a cooling chamber 148 and a threaded section 145 within trocar 122. Cooling chamber 148 may have a generally cylindrical shape and, additionally or alternatively, may have a stepped, tapered, conical, or other shape that is generally dimensioned in accordance with the shape of the tapered end 120 of the cylindroconical profile of trocar 122 to permit the flow of coolant to more effectively reach the distal regions of trocar 122. Additionally or alternatively, cooling chamber may have a square, hexagonal, or any suitable shape. Additionally, the dielectric properties of sterile water or saline flowing through cooling chamber 148 may enhance the overall ablation pattern of antenna 100. A coolant inflow tube 126 is in operable fluid communication at a proximal end thereof with a source of cooling fluid (not explicitly shown), and, at a distal end thereof, coolant inflow tube 126 is in fluid communication with cooling chamber 146 to provide coolant thereto. Coolant inflow tube 126 may be formed from any suitable material, e.g., a polymeric material, such as without limitation, polyimide. In an embodiment, coolant inflow tube 126 passes through coolant inflow port 131. In some embodiments, a coolant outflow channel 136 may be provided to facilitate removal of coolant from cooling chamber 146, through antenna assembly 100, to a collection reservoir (not explicitly shown). The coolant may be any suitable fluid, such as without limitation water, sterile water, deionized water, and/or saline.

Figure 4A:
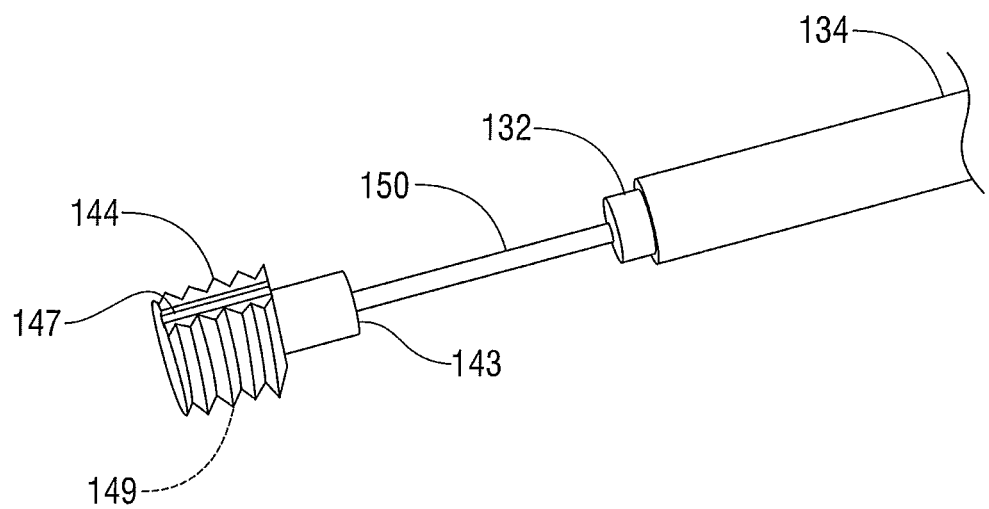
FIGS. 4A-4D show perspective views of a embodiment of a distal portion of a microwave antenna in various stages of assembly in accordance with an embodiment of the present disclosure.

Threaded section 145 of trocar 122 is configured to receive trocar screw 144. Trocar screw 144 includes at the proximal end thereof an opening 143 defined therein that is configured to accept the distal end of inner coaxial conductor 150. In embodiments, distal end of inner coaxial conductor 150 is fixed within opening 143 by any suitable manner of electromechanical attachment, such as without limitation welding, brazing, and/or crimping. As seen in FIG. 4A, an inflow groove 147 and an outflow groove 149 are disposed longitudinally through the threaded portion of trocar screw 144 to respectively facilitate the flow of coolant into, and out of, cooling chamber 148. Inflow groove 147 and outflow groove 149 may be configured to accommodate the insertion of coolant inflow tube 126 and/or a corresponding outflow tube (not explicitly shown). A return path 156 in the antenna assembly may additionally or alternatively provide an exit conduit for the cooling fluid.

In the illustrated embodiment, trocar 122 and proximal antenna member 128 include a dielectric coating 121, 127, respectively, on the respective outer surfaces thereof. The dielectric coating 121, 127 may include any suitable dielectric material, such as without limitation, ceramic material. In some embodiments, dielectric coating 121, 127 may be formed from titanium dioxide and/or zirconium dioxide. Dielectric coating 121, 127 may be applied to trocar 122 and/or proximal antenna member 128 by any suitable process, for example without limitation, plasma spraying or flame spraying. In embodiments, dielectric coating 121, 127 has a thickness in the range of about 0.005 inches to about 0.015 inches. During an ablation procedure, the dielectric coating 121, 127 may provide improved dielectric matching and/or improved dielectric buffering between the antenna and tissue, which may enable the use of higher power levels, which, in turn, may enable a surgeon to achieve greater ablation rates resulting in increased ablation size, reduced operative times, and/or improved operative outcomes.

An outer jacket 124 is disposed about the outer cylindrical surface of antenna assembly 100, e.g., the distal radiating portion 105, puck 130, and proximal radiating section 140. Outer jacket 124 may be formed from any suitable material, including without limitation polymeric or ceramic materials. In some embodiments, outer jacket 124 is formed from PTFE. Outer jacket 124 may be applied to antenna assembly 100 by any suitable manner, including without limitation, heat shrinking.

Continuing with reference to FIGS. 4A-4D, a method of manufacturing antenna assembly 100 is disclosed wherein inner coaxial conductor 150 is inserted into opening 143 of trocar screw 144. Inner coaxial conductor 150 is electrically fixed to trocar screw 144 by any suitable manner of bonding, such as without limitation, laser welding, brazing, or crimping. The coaxial transmission line 138 and trocar screw 144 subassembly is placed in a mold (not explicitly shown), such as without limitation an injection micro-mold, that is configured to overmold the puck 130. Advantageously, inflow groove 147 and outflow groove 149 are aligned with mold features (not explicitly shown) corresponding to coolant inflow port 131 and coolant outflow port 133 such that, when molded, a continuous fluid connection is formed between inflow groove 147 and coolant inflow port 131, and between outflow groove 149 and outflow port 133.

Figure 4B:
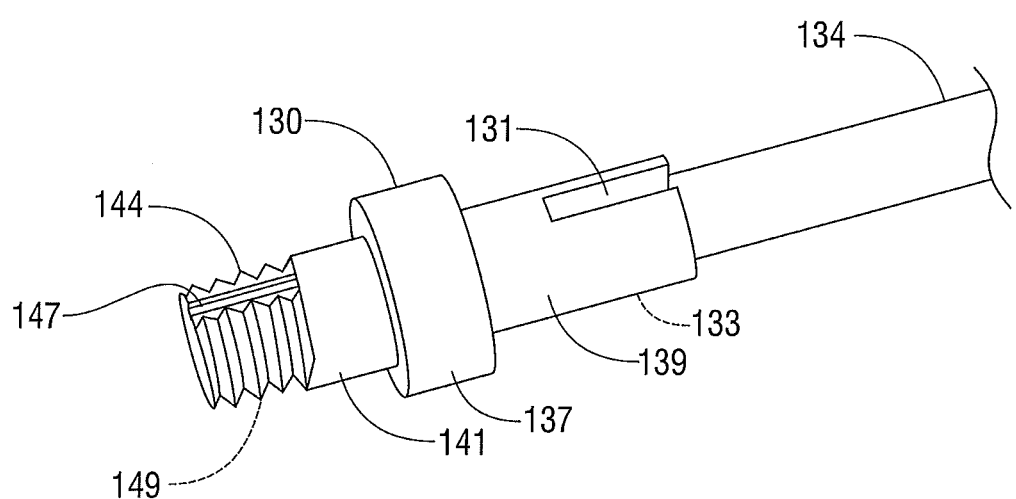

Puck material, e.g., ceramic, Pebax®, Ultem®, Extem®, Vespel®, or any suitable polymer having dielectric properties, is shot into the mold, allowed to cool/and or set, and subsequently released from the mold to form an assembly that includes puck 130, trocar screw 143 and coaxial transmission line 138 as best illustrated in FIG. 4B. The formed puck 130 includes a center section 137 having an outer diameter corresponding to the outer diameters of trocar 122 (inclusive of the thickness of dielectric coating 121) and/or proximal antenna member 128 (inclusive of the thickness of dielectric coating 127). Puck 130 further includes a distal shoulder 141 having an outer diameter corresponding to the inner diameter of trocar 122, and a proximal shoulder 139 having an outer diameter corresponding to the inner diameter of proximal antenna member 128.

Figure 4C:
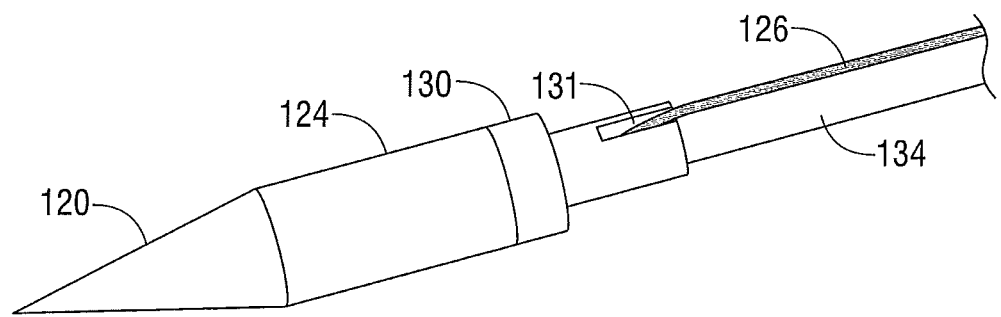
Figure 4D:
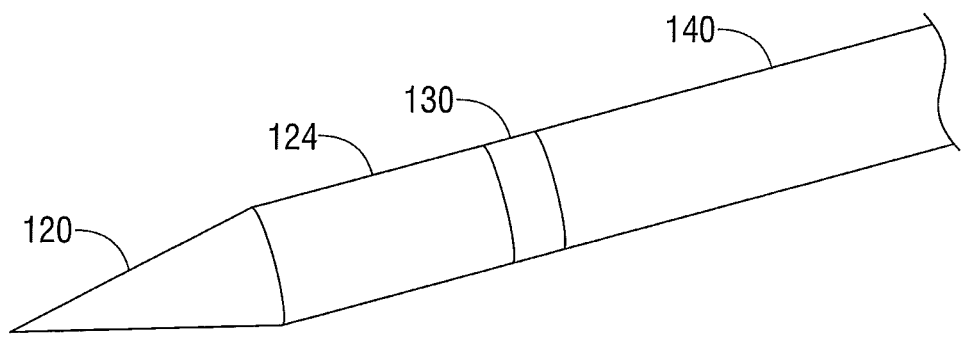
Figure 5:
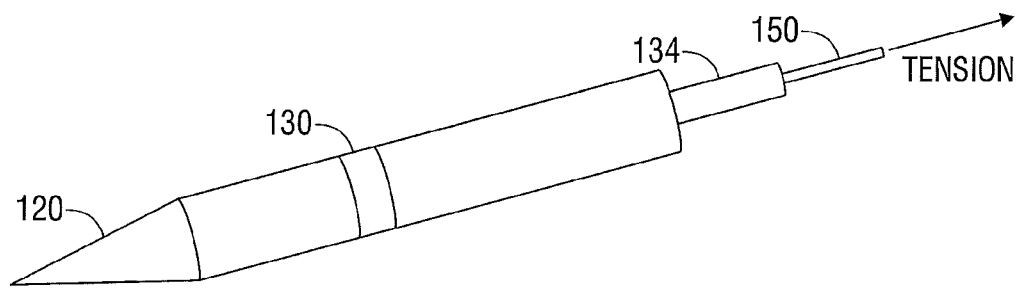
FIG. 5 shows a perspective view of an embodiment of a microwave antenna coupler having a tensioned inner conductor in accordance with an embodiment of the present disclosure.

Trocar 122 may then be threaded onto trocar screw 144 to form the distal radiating section 120, as best shown in FIG. 4C. Inflow tube 126 may then be inserted into coolant inflow port 131. Proximal antenna member 128 may then be positioned against puck 130 such that the distal end of proximal antenna member 128 engages the proximal shoulder of puck 130, thus forming a sealed proximal radiation section 140.

Tension may be applied to inner coaxial conductor 150 and/or dielectric 132 in a proximal direction, thereby drawing together distal radiating section 105, puck 130, and proximal radiating section 140, and placing puck 130 in a state of compression. Inner coaxial conductor 150 and/or dielectric 132 may be fixed in a state of tension at an anchor point 151, by any suitable manner of fixation, including without limitation spot welding, brazing, adhesive, and/or crimping. In this manner, the antenna sections are "locked" together by the tensile force of inner coaxial conductor 150 and/or dielectric 132, which may result in improved strength and stiffness of the antenna assembly.

Outer jacket 124 may be applied to the outer surface of radiating portion 12 by any suitable method, for example without limitation, heat shrinking, overmolding, coating, spraying, dipping, powder coating, baking and/or film deposition.

It is contemplated that the steps of a method in accordance with the present disclosure can be performed in a different ordering than the ordering provided herein.

Figure 6A:
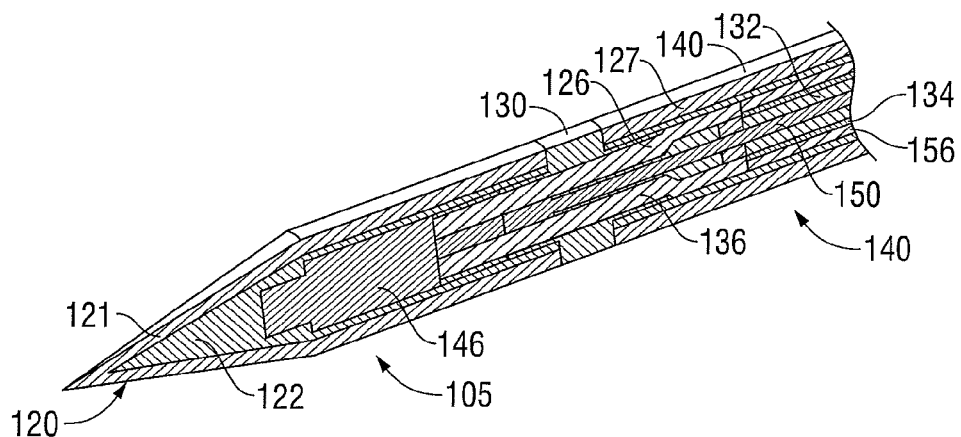
FIGS. 6A-6B show cross-sectional views of a distal end of a microwave antenna in accordance with an embodiment of the present disclosure.
Figure 6B:
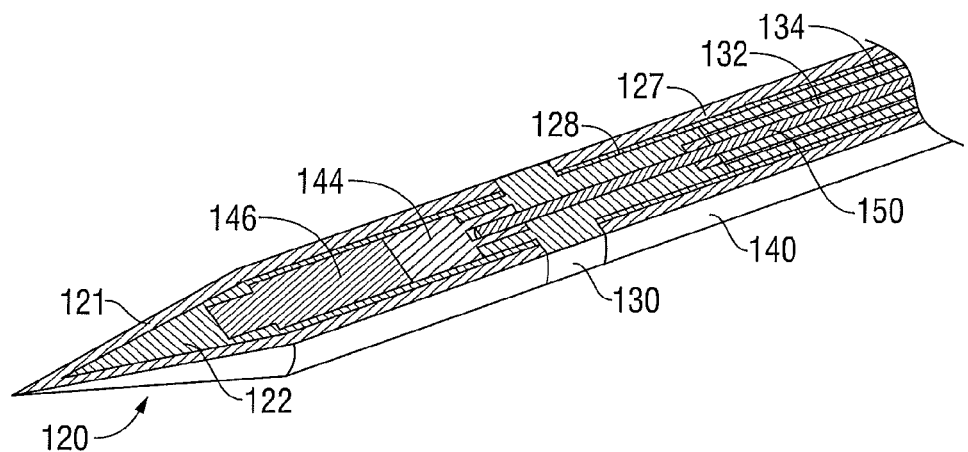

Turning now to FIGS. 6A and 6B, views of a distal end of a microwave antenna in accordance with an embodiment of the present disclosure are presented wherein FIG. 6A illustrates a cross-sectional view taken in a plane which exposes, inter alia, coolant inflow tube 126 and coolant outflow channel 136. FIG. 6B exposes a plane oriented approximately perpendicular to that of FIG. 6A, which illustrates, inter alia, a relationship between trocar screw 144, inner conductor 150, and puck 130.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A method of manufacturing a surgical antenna, comprising the steps of:
   providing a trocar screw adapted to receive a conductor at the proximal end thereof;
   electrically bonding a conductor to the trocar screw;
   positioning the trocar screw into a mold configured to overmold a puck thereupon;
   injecting puck material into the mold;
   allowing the puck material to set to form a puck assembly;
   releasing the puck assembly from the mold;
   providing a trocar adapted at the proximal end thereof to couple to the trocar screw;
   electrically coupling the trocar to the trocar screw to form a distal radiating section;
   providing a proximal antenna member adapted at the distal end thereof to couple to the puck assembly; and coupling the proximal antenna member to the puck assembly such that the conductor passes longitudinally through the proximal antenna member and exits at a proximal end thereof.

2. The method in accordance with claim 1, further comprising the steps of:
tensioning the conductor to draw together the distal radiating section, puck assembly, and proximal antenna member under compression to form an antenna assembly; and
fixing the conductor in relation to the proximal antenna member to maintain the stiffness of the antenna assembly.

3. The method in accordance with claim 1, wherein the bonding of the conductor to the trocar screw is achieved by at least one of welding, soldering, and crimping.

4. The method in accordance with claim 1, wherein the mold is further configured to form at least one of an inflow groove and an outflow groove in the puck assembly.

5. The method in accordance with claim 4, further comprising the step of inserting an inflow tube into an inflow slot.

6. The method in accordance with claim 4, further comprising the step of inserting an outflow tube into an outflow slot.

7. The method in accordance with claim 1, further comprising the step of applying an outer jacket to the antenna assembly.

* * * * *